US012297302B2

(12) United States Patent
Imase et al.

(10) Patent No.: US 12,297,302 B2
(45) Date of Patent: May 13, 2025

(54) AMPHIPHILIC COMPOUND, AND MEDICAL RESIN COMPOSITION AND PHARMACEUTICAL ADDITIVE USING THE SAME

(71) Applicant: Nippon Shokubai Co., Ltd., Osaka (JP)

(72) Inventors: Masato Imase, Osaka (JP); Akane Sato, Osaka (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 904 days.

(21) Appl. No.: 17/441,859

(22) PCT Filed: Mar. 30, 2020

(86) PCT No.: PCT/JP2020/014668
§ 371 (c)(1),
(2) Date: Sep. 22, 2021

(87) PCT Pub. No.: WO2020/203998
PCT Pub. Date: Oct. 8, 2020

(65) Prior Publication Data
US 2022/0185918 A1    Jun. 16, 2022

(30) Foreign Application Priority Data

Mar. 29, 2019   (JP) ................. 2019-067826

(51) Int. Cl.
*C08F 20/20* (2006.01)
*A61K 9/127* (2006.01)
*A61K 47/32* (2006.01)

(52) U.S. Cl.
CPC .............. *C08F 20/20* (2013.01); *A61K 9/127* (2013.01); *A61K 47/32* (2013.01)

(58) Field of Classification Search
CPC ......... C08F 216/02; C08F 16/02; C08F 20/20
See application file for complete search history.

(56) References Cited

U.S. PATENT DOCUMENTS

| | | | | |
|---|---|---|---|---|
| 4,071,508 A * | 1/1978 | Steckler | ................ | C08F 220/20 |
| | | | | 526/260 |
| 4,855,369 A * | 8/1989 | Yezrielev | .............. | C08F 220/12 |
| | | | | 526/213 |
| 11,160,755 B2 * | 11/2021 | Kim | ..................... | C08F 293/005 |
| 2002/0082372 A1 | 6/2002 | Leboeuf | | |
| 2011/0172314 A1 | 7/2011 | Findlay et al. | | |
| 2013/0046052 A1 | 2/2013 | Armes et al. | | |
| 2020/0323775 A1 * | 10/2020 | Kim | ..................... | C08F 293/00 |

FOREIGN PATENT DOCUMENTS

| | | |
|---|---|---|
| CN | 1371481 A | 9/2002 |
| CN | 102099387 A | 6/2011 |
| JP | H10-506127 A | 6/1998 |
| JP | 2003-508125 A | 3/2003 |
| JP | 2010-531166 A | 9/2010 |
| JP | 2013-23571 A | 2/2013 |
| WO | 2001/016626 A1 | 3/2001 |
| WO | 03047499 A2 | 6/2003 |
| WO | 2008/084656 A1 | 7/2008 |

OTHER PUBLICATIONS

Office Action dated Aug. 2, 2022 for the corresponding Japanese Patent Application No. 2021-512133, with English translation.
Office Action dated Jul. 27, 2022 for the corresponding Chinese Patent Application No. 202080024959.2, with English translation.
PCT, International Search Report for the corresponding patent application No. PCT/JP2020/014668, dated Jun. 23, 2020, with English translation.
Els T. M. Dams, et al., "Accelerated Blood Clearance and Altered Biodistribution of Repeated Injections of Sterically Stabilized Liposomes," The Journal of Pharmacology and Experimental Therapeutics, 2000, pp. 1071-1079, vol. 292, No. 3.
Yoshihisa Kaneda, et al., "The use of PVP as a polymeric carrier to improve the plasma half-life of drugs," Biomaterials, 2004, pp. 3259-3266, vol. 25, No. 16.
First Office Opinion Notice, dated Jul. 18, 2024, for the Corresponding Chinese Patent Application No. 202310509657.X, with English Translation.
Zhou, Chengfei, "Research progress on the synthesis of macromonomers and their application in radiation polymerization ÿ. Synthesis of macromonomers", Synthetic Technology and Application, vol. 27, Issue 4, pp. 26-32, Dec. 28, 2012, with English Translation.
Blanaz, A., et al., "Predictive Phase Diagrams for RAFT Aqueous Dispersion Polymerization: Effect of Block Copolymer Composition, Molecular Weight, and Copolymer Concentration", Macromolecules, vol. 45, pp. 5099-5107, Jun. 13, 2012.
JPO, Japanese Office Action mailed Apr. 23, 2024 for the related Japanese application No. 2023-045195, with English translation, 8 pages.
Bai Yuhao, et al. "Preparation of Diblock Copolymer Nano-objects by Aqueous Photoinitiated Polymerization-induced Self-assembly[J]", Imaging Science and Photochemistry, Jan. 1, 2017, 35(6): 816-823, with a partial translation.

(Continued)

*Primary Examiner* — Margaret G Moore
(74) *Attorney, Agent, or Firm* — LUCAS & MERCANTI, LLP (57) ABSTRACT

Provided is means capable of reducing the adsorptivity to plastics while suppressing a decrease in intracellular uptake efficiency in an amphiphilic compound that can be applied to long-term blood-retaining liposomes or the like as a drug carrier. The above problem can be solved by an amphiphilic compound comprising a moiety (I) including a constitutional unit (A) derived from a monomer (a) having two or more hydroxyl groups and having 2 to 10 carbon atoms constituting the side chain among the carbon atoms of the constitutional unit, and a hydrocarbon group having 8 or more carbon atoms.

17 Claims, 4 Drawing Sheets

(56) References Cited

OTHER PUBLICATIONS

Jones Marie-Christine, et al. "Self-Assembled Nanocages for Hydrophilic Guest Molecules", Journal of the American Chemical Society Nov. 15, 2006 128 (45), 14599-14605 DOI: 10.1021/ja065462c.

EPO, "European Search Report", issued in connection with related European patent application No. 20781875.8 and dated Dec. 6, 2022 (7 pages).

Office Action, dated Sep. 17, 2024, issued for the corresponding Japanese Patent Application No. 2023-045195, 8 pages, with English Translation.

Office Action, dated Nov. 22, 2024, which was issued for the corresponding Canadian Patent Application No. 3,134,852, 4 pages.

\* cited by examiner

FIG. 4

AMPHIPHILIC COMPOUND, AND MEDICAL RESIN COMPOSITION AND PHARMACEUTICAL ADDITIVE USING THE SAME

CROSS REFERENCE TO RELATED APPLICATION

This Application is a 371 of PCT/JP2020/014668 filed on Mar. 30, 2020 which, in turn, claimed the priority of Japanese Patent Application No. 2019-067826 filed on Mar. 29, 2019, both applications are incorporated herein by reference.

TECHNICAL FIELD

The present invention relates to an amphiphilic compound, and a medical resin composition and a pharmaceutical additive using the same.

BACKGROUND ART

In recent years, a preparation (DDS preparation) based on a drug delivery system (that is, a drug delivery system (DDS)) has been actively developed. Recent DDS preparations include preparations that facilitate the accumulation of a molecular-targeted therapeutic agent in active targeting therapy and medicines in target cells by nanotechnology in passive targeting therapy.

Polyethylene glycol (PEG: PolyEthylene Glycol) has been widely used as a substance used in this passive targeting therapy.

For example, PEG-modified liposomes obtained by modifying liposomes or high molecular weight micelles with PEG are used as long-term blood-retaining liposomes as drug carriers, a preparation containing doxorubicin (Doxil (registered trademark)), and the like have been clinically used.

PEG is highly flexible due to the simple skeletal structure thereof. In addition, since it has the property of being able to hydrate many water molecules, a heavy hydrated layer is formed on the surface layer of the particles by modifying the drug particles and carriers with PEG. It has been known that this hydrated layer suppresses the interaction with serum proteins and cells, and as a result, the blood (internal) residence time of the drug is greatly extended (stealthization).

As described above, PEG-modified pharmaceuticals are expected to continue to play an important role in new preparation technology, and many of them are still in clinical trials. However, in recent years, it has been reported that in liposomes and high molecular weight micelles surface-modified with PEG, a phenomenon (Accelerated Blood Clearance: ABC phenomenon) in which the stealth property of a drug is lost due to repeated administration (frequent administration) occurs (Non-Patent Literature 1).

This ABC phenomenon means that a pharmacological effect associated with frequent administration may be reduced and an unexpected side effect may be induced. Therefore, it is expected that such PEGylated pharmaceuticals will be subject to restrictions on the types of indications and drug administration modes (dose/frequency/frequency of administration) in the future, and it is strongly desired to overcome this problem.

So far, attempts have been made to suppress the occurrence of the ABC phenomenon by producing a modified pharmaceutical using a modifying agent instead of PEG. For example, a technique for imparting stealth to a protein drug by using polyvinylpyrrolidone (PVP) as a modifier as polymer alternative to PEG has been reported (Non-Patent Literature 2).

CITATION LIST

Non-Patent Literatures

Non-Patent Literature 1: J. Pharmacol. Exp. Ther., 292 (3): 1071-1079 (2000)
Non-Patent Literature 2: Biomaterials, 25 (16): 3259-3266 (2004)

SUMMARY OF INVENTION

Technical Problem

The present inventors have been developing an amphiphilic compound having a hydrophilic portion and a hydrophobic portion in a molecule, mainly on the premise of application to long-term blood-retaining liposomes or the like as drug carriers. Then, in the study at that time, the present inventors have found that PVP exhibits high adsorptivity to plastics such as polypropylene (PP). Here, polypropylene (PP) has been widely used as a constituent material for a syringe of an injector. For this reason, for example, assuming that when polymer-modified liposomes are used as drug carriers to construct injection solutions and prefilled syringes, or an injection solution or a prefilled syringe is formed by using a polymer modified protein as an active component, for example, there is a problem in that liposomes containing the active component are adsorbed on the inner wall of the syringe via PVP, and a part of the active component contained in the liposome remains in the syringe without being administered. Further, PEG-modified liposomes known in the related art have a problem in that intracellular uptake efficiency is lowered.

Therefore, an object of the present invention is to provide means capable of reducing the adsorptivity to plastics while suppressing a decrease in intracellular uptake efficiency in an amphiphilic compound that can be applied to long-term blood-retaining liposomes or the like as a drug carrier.

Solution to Problem

The present inventors have conducted diligent studies in view of the above problems. As a result, it has been found that the above problems can be solved by using an amphiphilic compound containing a moiety (in this specification, it is also simply referred to as "moiety (I)") including a constitutional unit derived from the monomer having two or more hydroxyl groups in the molecule and having 2 to 10 carbon atoms constituting the side chain among the carbon atoms of the constitutional unit, and a hydrocarbon group having 8 or more carbon atoms in the molecule, and thereby the present invention has been completed.

That is, according to one embodiment of the present invention, there is provided an amphiphilic compound containing a moiety (I) including a constitutional unit (A) derived from a monomer (a) having two or more hydroxyl groups and having 2 to 10 carbon atoms constituting the side chain among the carbon atoms of the constitutional unit, and a hydrocarbon group having 8 or more carbon atoms.

According to the present invention, it is possible to reduce the adsorptivity to plastics while suppressing a decrease in intracellular uptake efficiency in an amphiphilic compound that can be applied to long-term blood-retaining liposomes or the like as a drug carrier.

DESCRIPTION OF EMBODIMENTS

According to one embodiment of the present invention, there is provided an amphiphilic compound containing a moiety (I) including a constitutional unit (A) derived from a monomer (a) having two or more hydroxyl groups and having 2 to 10 carbon atoms constituting the side chain among the carbon atoms of the constitutional unit, and a hydrocarbon group having 8 or more carbon atoms.

The moiety (I) of the amphiphilic compound having such a structure has lower adsorptivity to plastics such as PP as compared with PVP. Therefore, the compound can be applied to long-term blood-retaining liposomes and the like as a drug carrier while reducing the adsorptivity to plastics. As a result, for example, it is possible to reduce the possibility that the active component encapsulated in the liposome modified with the compound as a drug carrier remains in the syringe. In addition, it is possible to significantly suppress a decrease in the intracellular uptake efficiency as seen in PEG-modified liposomes.

Although the mechanism by which the amphiphilic compound according to the present invention can exhibit excellent performance when used in the above-mentioned applications, for example, has not been completely clarified, a mechanism such as hydrophobic adsorption has been presumed. Note that, the above mechanism is presumed, and the present invention is not limited to the above mechanism.

Hereinbelow, preferable embodiments of the present invention are described. However, the present invention is not limited to the following embodiments. Furthermore, a combination of two or more of the individual preferable embodiments of the invention described below is also a preferable embodiment of the invention.

In the present specification, "X to Y" indicating a range means "X or more and Y or less", and "weight" and "mass" are treated as synonyms. Further, in the present specification, "(meth)acrylate" means acrylate or methacrylate, "(meth)acrylic" means acrylic or methacrylic, and acrylate and methacrylate may be used alone, or may be used in combination. Unless otherwise specified, measurements of operations, physical properties, and the like are performed under the conditions of room temperature (20 to 25° C.)/ relative humidity 40 to 50% RH.

Amphiphilic Compound

An amphiphilic compound according to the present embodiment has a moiety (I) including a constitutional unit (A) having a predetermined structure and a hydrocarbon group having 8 or more carbon atoms. Hereinafter, these components will be described in detail.

(Moiety (I))

The amphiphilic compound according to the present invention first contains a moiety (I) including a constitutional unit (A) derived from a monomer (a) having two or more hydroxyl groups and having 2 to 10 carbon atoms constituting the side chain among the carbon atoms of the constitutional unit. In a preferable embodiment, the moiety (I) consists of a polymer having a constitutional unit (A) derived from a monomer (a) having two or more hydroxyl groups and having 2 to 10 carbon atoms constituting the side chain among the carbon atoms of the constitutional unit. Here, in the present specification, "a structural unit (Q) derived from a monomer (P)" (P represents an optional appropriate code, and the notation of (P) may not be provided) typically means that one of the bonds of the polymerizable unsaturated double bond of the "monomer (P)" (or simply referred to as "monomer") is opened by polymerization and becomes a unit (Q) (Q represents an optional appropriate code, and the notation of (Q) may not be provided) constituting at least a part of the polymer. The above-mentioned "structural unit derived from monomer (P)" may be a structural unit formed by another producing method as long as it has the same structure as the structural unit (in the specific example shown below, the structural unit represented by the general formula (Q)) formed by polymerizing a monomer (P) (or simply referred to as "monomer") as described above. For example, the structural unit formed by polymerizing the hydroxyl group-protected monomer (a) may be deprotected to form the constitutional unit (A). For example, a structural unit derived from glycerin (meth) acrylate may be formed by polymerizing (2-methyl-2-ethyl-1,3-dioxolan-4-yl) methyl (meth)acrylate or glycidyl ether (meth)acrylate and hydrolyzing.

The monomer (a) having two or more hydroxyl groups and having 2 to 10 carbon atoms constituting the side chain among the carbon atoms of the constitutional unit is preferably a vinyl monomer, and is more preferably a (meth) acrylic monomer. Further, the monomer (a) may be a monofunctional monomer or a polyfunctional monomer, and preferably contains a monofunctional monomer and more preferably, it consists of a monofunctional monomer.

Here, as the (meth)acrylic monomer as the monomer (a), (meth)acrylates such as glycerin mono (meth)acrylate (also known as 2,3-dihydroxypropyl (meth)acrylate), 1,2-dihydroxyethyl (meth)acrylate, 2,2-dihydroxyethyl (meth)acrylate, dihydroxybutyl (meth)acrylate, trimethylolpropane mono (meth)acrylate, pentaerythritol mono (meth)acrylate, and dipentaerythritol mono (meth)acrylate are preferably used. Among these, glycerin monoacrylate (GLMA) or glycerin monomethacrylate (GLMMA) is preferable from the viewpoint of easy industrial availability and high reactivity. By polymerizing these (meth)acrylic monomers (a), an ethylenic double bond contained in the monomer (a) is cleaved to generate the constitutional unit (A). Note that, the monomer (a) may be used alone, or two or more kinds thereof may be used in combination.

Further, among the carbon atoms of the constitutional unit derived from the monomer (a), the number of carbon atoms constituting the side chain is 2 to 10, but in the present specification, the term "side chain" refers to a portion other than the main chain that includes the constitutional unit. The "main chain" means a chain of continuously bonded carbon atoms in a polymer consisting of a series of constitutional units, which has the largest number of carbon atoms. However, exceptionally, when the monomer (a) is a methacrylic monomer, it is assumed that the methyl group bonded to the carbon atom constituting the unsaturated double bond in the monomer does not form a main chain or a side chain. As described above, As mentioned above, among the carbon atoms of the constitutional unit derived from the monomer (a), the number of carbon atoms constituting the side chain is 2 to 10, and the number of carbon atoms is preferably 3 to 8 and more preferably 4 to 6.

Here, the constitutional unit (A) preferably includes a constitutional unit represented by the following chemical formula (1).

[Chem. 1]

(1)

In formula (1), $R^1$ represents a hydrogen atom or a methyl group, and preferably a hydrogen atom. In addition, X represents —C(=O)—O—, —C(=O)—NH—, —O—, —CH$_2$O—, or —CH$_2$CH$_2$O—, and preferably —C(=O)—O—.

Among the constitutional units represented by the above chemical formula (1), those in which $R^1$ is a hydrogen atom and X is —C(=O)—O— are derived from glycerin monoacrylate (GLMA) as the monomer (a). In addition, among the constitutional units represented by the above chemical formula (1), those in which $R^1$ is a methyl group and X is —C(=O)—O— are derived from glycerin monomethacrylate (GLMMA) as the monomer (a).

The proportion of the constitutional unit (A) derived from the monomer (a) having two or more hydroxyl groups in the molecule and having 2 to 10 carbon atoms constituting the side chain among the carbon atoms of the constitutional unit, which occupies the moiety (I) constituting the amphiphilic compound is, for example, 1 to 100% by mass, preferably 20 to 100% by mass, more preferably 50 to 100% by mass, further preferably 60 to 100% by mass, still more preferably 80 to 100% by mass, particularly preferably 90 to 100% by mass, and most preferably 100% by mass. If the proportion of the constitutional unit (A) is a value within the above range, the action and effect of the present invention can be exhibited.

When the moiety (I) constituting the amphiphilic compound contains a constitutional unit other than the constitutional unit (A) (hereinafter, also simply referred to as "constitutional unit (B)") the constitutional unit (B) may be derived from optional radically polymerizable monomer (hereinafter, a monomer that becomes a constitutional unit (B) by copolymerization is also referred to as "monomer (b)"). When the moiety (I) constituting the amphiphilic compound contains the constitutional unit (B), the proportion of the constitutional unit (B) to the moiety (I) is, for example, 99% by mass or less, preferably 80% by mass or less, more preferably 50% by mass or less, further preferably 40% by mass or less, still more preferably 20% by mass or less, and particularly preferably 10% by mass or less.

Examples of the monomer (b) include those other than the monomer (a) such as hydroxyl group-containing (meth)acrylate, a polyoxyalkylene group-containing monomer, alkoxyalkyl (meth)acrylate, a vinyl monomer, alkylene oxide, alkoxypolyoxyalkylene glycol, a cyclic compound, and amino acid (such as aspartic acid or glutamic acid). The monomers (b) may be also used alone, or two or more kinds thereof may be used in combination.

Examples of the hydroxyl group-containing (meth)acrylate include hydroxyalkyl (meth)acrylate having 2 to 4 carbon atoms in a hydroxyalkyl group such as 2-hydroxyethyl acrylate, 2-hydroxyethyl methacrylate, and the like.

Examples of the polyoxyalkylene group-containing unsaturated monomer include a monomer represented by the following chemical formula (2) or the like.

[Chem. 2]

(2)

In formula (2), $R^2$, $R^3$, and $R^4$ each independently represents a hydrogen atom or a methyl group, $R^5$ represents an alkylene group having 2 to 18 carbon atoms, $R^6$ represents a hydrogen atom or a hydrocarbon group having 1 to 20 carbon atoms, X represents a direct bond when an alkylene group having 1 to 5 carbon atoms, a —CO— group, or a $R^2R^4C=CR^3$— group is a vinyl group, and m represents the average number of added moles of a —($R^5$O)— group and represents a number from 1 to 300. In the formula (2), when $(R^5O)_m$ consists of two or more kinds of $R^5$O, the two or more kinds of $R^5$O may be in any of random, block, and alternate binding forms.

In the formula (2), $R^6$ is a hydrogen atom or a hydrocarbon group having 1 to 20 carbon atoms. Among $R^6$, a hydrogen atom and a hydrocarbon group having 1 to 20 carbon atoms are preferable, a hydrocarbon group having 1 to 10 carbon atoms is more preferable, a hydrocarbon group having 1 to 3 carbon atoms is further preferable, and a hydrocarbon group having 1 or 2 carbon atoms is still more preferable. Among the hydrocarbon groups, an alkyl group or an alkenyl group is preferable, an alkyl group having 1 to 20 carbon atoms is more preferable, an alkyl group having 1 to 10 carbon atoms is further preferable, and an alkyl group having 1 to 3 carbon atoms is still more preferable.

In the formula (2), an oxyalkylene group represented by the formula: —$R^5$O— is an oxyalkylene group having 2 to 18 carbon atoms. Examples of the oxyalkylene group include an oxyethylene group, an oxypropylene group, an oxybutylene group, an oxyisobutylene group, an oxy-1-butene group, an oxy-2-butene group, and the like. Among these oxyalkylene groups, an oxyalkylene group having 2 to 8 carbon atoms is preferable, and an oxyalkylene group having 2 to 4 carbon atoms such as an oxyethylene group, an oxypropylene group, and an oxybutylene group is more preferable, and an oxyethylene group further preferable.

In the chemical formula (2), m is the average number of added moles of the oxyalkylene group represented by the formula: —$R^5O$—. The average number of added moles means the average number of moles of oxyalkylene groups in 1 mole of a polyoxyalkylene group-containing unsaturated monomer. A lower limit of m is preferably 2 or more, more preferably 4 or more, and further preferably 8 or more. An upper limit of m is preferably 100 or less and more preferably 50 or less.

X represents a direct bond when the alkylene group, a —CO— group, or $R^2R^4C=CR^3$— group having 1 to 5 carbon atoms is a vinyl group. Among these groups, the —CO— group is preferable.

Examples of the polyoxyalkylene group-containing unsaturated monomer include an unsaturated alcohol polyalkylene glycol adduct, a polyalkylene glycol ester monomer, (alkoxy) polyalkylene glycol monomaleic acid ester, and the like.

An unsaturated alcohol polyalkylene glycol adduct is a compound in which a polyalkylene glycol chain is added to alcohol having an unsaturated group. Examples of the unsaturated alcohol polyalkylene glycol adduct include polyethylene glycol monovinyl ether, polyethylene glycol monoallyl ether, polyethylene glycol mono (2-methyl-2-propenyl) ether, polyethylene glycol mono (2-butenyl) ether, polyethylene glycol mono (3-methyl-3-butenyl) ether, polyethylene glycol mono (3-methyl-2-butenyl) ether, polyethylene glycol mono (2-methyl-3-butenyl) ether, polyethylene glycol mono (2-methyl-2-butenyl) ether, polyethylene glycol mono (1,1-dimethyl-2-propenyl) ether, polyethylene polypropylene glycol mono (3-methyl-3-butenyl) ether, methoxypolyethylene glycol mono (3-methyl-3-butenyl) ether, and the like.

The polyalkylene glycol ester-based monomer is a monomer in which an unsaturated group and a polyalkylene glycol chain are bonded via an ester bond.

As the polyalkylene glycol ester-based monomer, for example, an esterified product of alkoxypolyalkylene glycol having 1 to 300 mol of an oxyalkylene group having 2 to 18 carbon atoms added to an alcohol and (meth) acrylic acid is preferable. Among the alkoxypolyalkylene glycols, those containing an oxyethylene group as a main component are preferable. Examples of the alcohol include aliphatic alcohols having 1 to 30 carbon atoms such as methanol, ethanol, 1-propanol, 2-propanol, 1-butanol, 2-butanol, 1-pentanol, 2-pentanol, 3-pentanol, 1-hexanol, 2-hexanol, 3-hexanol, octanol, 2-ethyl-1-hexanol, nonyl alcohol, lauryl alcohol, cetyl alcohol, and stearyl alcohol; alicyclic alcohols having 3 to 30 carbon atoms such as cyclohexanol; unsaturated alcohols having 3 to 30 carbon atoms such as (meth)allyl alcohol, 3-buten-1-ol, and 3-methyl-3-buten-1-ol, and the like. Examples of the esterified product include methoxypolyethylene glycol mono (meth)acrylate, methoxy (polyethylene glycol polypropylene glycol) mono (meth)acrylate, methoxy (polyethylene glycol polybutylene glycol) mono (meth)acrylate, methoxy (polyethylene glycol polypropylene glycol polybutylene glycol) mono (meth)acrylate, and the like. Among the polyalkylene glycol ester-based monomers, (alkoxy) polyalkylene glycol mono (meth)acrylate such as methoxypolyethylene glycol monomethacrylate is preferable.

Examples of the alkoxyalkyl (meth)acrylate include alkoxyalkyl (meth)acrylates, in which an alkoxy group has 1 to 4 carbon atoms and an alkyl group has 1 to 4 carbon atoms, such as methoxymethyl (meth)acrylate, methoxyethyl (meth)acrylate, methoxypropyl (meth)acrylate, ethoxymethyl (meth)acrylate, ethoxyethyl (meth)acrylate, ethoxypropyl (meth)acrylate, and they like. These alkoxyalkyl (meth)acrylates may be used alone or in combination of two or more types thereof.

Examples of the vinyl monomer include (meth)acrylic acid, methyl (meth)acrylate, ethyl (meth)acrylate, propyl (meth)acrylate, n-butyl (meth)acrylate, isobutyl (meth)acrylate, tert-butyl (meth)acrylate, 2-ethylhexyl (meth)acrylate, n-lauryl (meth)acrylate n-stearyl (meth)acrylate, diaminomethyl (meth)acrylate, diaminoethyl (meth)acrylate, dimethylamino (meth)acrylate, diethylamino (meth)acrylate, glycidyl (meth)acrylate, styrene, aziridines, 2-(meth)acryloyloxymethylphosphorylcholine, 2-(meth)acryloyloxyethyl phosphorylcholine, tetrahydrofurfuryl (meth)acrylate, isopropylacrylamide, vinyl alcohol, vinylformamide, vinylisobutylacrylamide, (meth)acrylamide, dimethylacrylamide, vinylacetamide, N-vinylpyrrolidone, and the like.

Examples of the alkylene oxide include alkylene oxides having 2 to 4 carbon atoms such as ethylene oxide, propylene oxide, and the like.

Examples or the alkoxypolyoxyalkylene glycol include alkoxypolyoxyalkylene glycol, which has an alkoxy group having 1 to 4 carbon atoms and an oxyalkylene group having 1 to 4 carbon atoms in which the number of moles of the oxyalkylene group added is 2 to 30, such as polyethylene glycol, polypropylene glycol, methoxypolyethylene glycol, ethoxypolyethylene glycol, methoxypolypropylene glycol, and ethoxypolypropylene glycol, and the like.

Examples of the cyclic compound include lactides such as L-lactide, lactones such as ε-caprolactone, trimethyl carbonate, cyclic amino acid, morpholine-2,5-dione, and the like.

When the moiety (I) consists of a polymer having the constitutional unit (A), a polymer constituting the polymer may have a structure of a block copolymer obtained by bonding polymers of the same type or different types.

The number average molecular weight (Mn) of the polymer is preferably 1000 or more, more preferably 2000 or more, and further preferably 3000 or more from the viewpoint of adsorptivity or the like to the inner wall of the syringe. The number average molecular weight (Mn) of the polymer is preferably 90,000 or less, more preferably 30,000 or less, and further preferably 15,000 or less from the viewpoint of extracorporeal excretion or the like. The value of the number average molecular weight (Mn) of the polymer means the value when measured based on the method for measuring Mn of the polymers obtained in Production Examples 1 to 7, in examples described later. Here, in the examples described later, since the number average molecular weight (Mn) of the amphiphilic compound is measured, the Mn value of the moiety (I) (polymer) can be calculated by subtracting the molecular weight of the moiety other than the moiety (I) (polymer) from this measured value. If an accurate value can be calculated, the value of Mn may be obtained by the same method using only the moiety (I) (polymer).

The molecular weight distribution of the polymer (value of [polymerization average molecular weight (Mw)/number average molecular weight (Mn)]) is preferably 1 to 5, more preferably 1 to 3, further preferably 1 to 2, still more preferably 1 to 1.5, and even more preferably 1 to 1.3, from the viewpoint of modifying the amphiphilic compound (polymer) to liposomes or the like.

The polymer constituting the moiety (I) can be obtained by polymerizing a monomer composition containing the monomer (a) and, if necessary, a monomer (b). Examples of the method for polymerizing the above-mentioned monomer composition include a living radical polymerization method represented by, for example, a radical polymerization method, an atom transfer radical polymerization method, and a reversible addition-fragmentation chain transfer (RAFT) polymerization method, an ionic polymerization method, a ring-opening polymerization method, a coordination polymerization method, a polycondensation method, and the like, but the present invention as not limited to these examples.

When polymerizing the monomer composition, a solvent may be used. Examples of the solvent include aromatic solvents such as benzene, toluene, and xylene; alcohol-based solvents such as methanol, ethanol, isopropanol, n-butanol, and tert-butanol; halogen atom-containing solvents such as dichloroethane and dichloromethane; ether-based solvents such as diethyl ether, propylene glycol methyl ether, dipropylene glycol methyl ether, ethyl cellosolve, and butyl cellosolve; ester-based solvents such as ethyl acetate, butyl acetate, and cellosolve acetate; ketone-based solvents such as acetone, methyl ethyl ketone, methyl isobutyl ketone, and diacetone alcohol; organic solvents such as amide-based solvents such as dimethylformamide and water. These solvents may be used alone, or two or more kinds thereof may be used in combination. The amount of the solvent may be appropriately determined in consideration of the polymerization conditions, the composition of the monomer composition, the concentration of the obtained polymer, and the like.

When polymerizing the monomer composition, a chain transfer agent can be used to adjust the molecular weight of a polymer and to introduce a hydrocarbon group.

Examples of the chain transfer agent include hydrophilic thiol-based chain transfer agents such as alkali metal salts of thioacetate such as sodium thioacetate and potassium thioacetate, cysteine, cysteamine, mercaptoethanol, thioglycerol, thioglycolic acid, mercaptopropionic acid, 2-mercaptopropionic acid, 3-mercaptopropionic acid, thioacetic acid, thiomalic acid, 2-mercaptoethanesulfonic acid, sodium salts thereof, and potassium salt; non-thiol chain transfer agents such as primary alcohols such as 2-aminopropan-1-ol, secondary alcohols such as isopropanol, phosphite, hypophosphite, and salts thereof (for example, sodium hypophosphite, potassium hypophosphite, and the like), sulfites, hydrogen sulfites, dithionic acids, metabisulfites and salts thereof (for example, sodium sulfite, sodium hydrogen sulfite, sodium dithionate, sodium metabisulfite, potassium sulfite, potassium hydrogen sulfite, potassium dithionate, potassium metabisulfite, and the like); and hydrophobic thiol chain transfer agents such as butanethiol, octanethiol, decanethiol, dodecanethiol, hexadecane thiol, octadecane thiol, thiocholesterol, cyclohexyl mercaptan, thiophenol, octyl thioglycolate, octyl 2-mercaptopropionate, octyl 3-mercaptopropionate, mercaptopropionic acid 2-ethylhexyl ester, octanoic acid 2-mercaptoethyl ester, 1,8-dimercapto-3,6-dioxaoctane, decantrithiol, dodecyl mercaptan, and the like. In addition, when performing reversible additional cleavage chain transfer (RAFT) polymerization, it is necessary to use a reversible additional cleavage chain transfer (RAFT) agent as the chain transfer agent. Examples of such RAFT agent include 4-cyano-4-(phenylcarbonothioylthio) pentanoic acid, 2-cyano-2-propylbenzothioate, 2-cyano-2-propyldodecyltrithiocarbonate, 4-cyano-4-[(dodecylsulfanylthiocarbonyl) sulfanyl] pentanoic acid, 2-(dodecylthiocarbonothioylthio)-2-methylpropanoic acid, cyanomethyldodecylthiocarbonate, cyanomethylmethyl (phenyl) carbamothioate, bis(thiobenzoyl) disulfide, bis(dodecylsulfanylthiocarbonyl) disulfide, and the like. These chain transfer agents may be used alone, or two or more kinds thereof may be used in combination.

The amount of the chain transfer agent may be appropriately set according to the type of the monomer contained in the monomer composition, the polymerization conditions such as the polymerization temperature, the molecular weight of the target polymer, and the like, but it is not particularly limited. However, in a case of obtaining a polymer having a number average molecular weight of several thousand to tens of thousands, the amount of the chain transfer agent is preferably 0.1 to 20 parts by mass, and more preferably 0.5 to 15 parts by mass per 100 parts by mass of the monomer.

When polymerizing the monomer composition, a polymerization initiator can be used.

Examples of the polymerization initiator include radical polymerization initiators such as azobisisobutyronitrile, 2,2'-azobis(4-dimethoxy-2,4-dimethylvaleronitrile), 4,4'-azobis(4-cyanopentanoic acid), 2,2'-azobis[2-methyl-N-[1,1-bis(hydroxymethyl)-2-hydroxyethyl] propionamide], 2,2'-azobis[N-(2-hydroxyethyl)-2-methoxypropanamide], 2,2'-azobis(2-methyl-2-propenylpropanamide), 2,2'-bis(2-imidazolin-2-yl) [2,2'-azobispropane] dihydrochloride, 2,2'-azobis(propane-2-carboamidine) dihydrochloride, 2,2'-azobis[N-(2-carboxyethyl)-2-methylpropion amidine], 2,2'-azobis[2-[1-(2-hydroxyethyl)-2-imidazolin-2-yl] propane dihydrochloride, 2,2'-azobis(2,4-dimethylvaleronitrile), 2,2'-azobis(2-methylbutyronitrile), tert-butylperoxy-2-ethylhexanoate, 2,2'-azobis(isobutyronitrile), benzoyl peroxide, di-tert-butyl peroxide, cyclohexanone peroxide, and acetylacetone peroxide; and living radical polymerization initiators such as bromomethylbenzene, 1-(bromomethyl)-4-methylbenzene, ethyl 2-bromoisobutyrate, hydroxyethyl 2-bromoisobutyrate, bis[2-(2'-bromoisobutyryloxy) ethyl] disulfide, 2-bromoisobutyrate 10-undecenyl, 4-(1-bromoethyl) benzoic acid, and the like. These polymerization initiators may be used alone, or two or more kinds thereof may be used in combination.

The amount of the polymerization initiator may be appropriately set according to the desired physical properties of the obtained polymer and the like, and usually, the amount of the polymerization initiator is preferably 0.001 to 20 parts by mass, and more preferably 0.005 to 10 parts by mass per 100 parts by mass of the monomer.

The polymerization conditions for polymerizing the monomer composition may be appropriately set according to the polymerization method, and are not particularly limited. The polymerization temperature is preferably room temperature to 200° C., and more preferably 40 to 140° C. The atmosphere for polymerizing the monomer composition is preferably an inert gas such as nitrogen gas or argon gas. The reaction time may be appropriately set so that the polymerization reaction of the monomers is completed.

By polymerizing, preferably, the monomer composition as described above, a polymer constituting the moiety (I) can be obtained. Here, the obtained polymer may have a functional group at the terminal thereof. When the polymer constituting the moiety (I) has a functional group at the terminal thereof, it is possible to easily modify a medicine or the like via the functional group, or to link it with a predetermined hydrocarbon group described later via the functional group. Here, the polymer constituting the moiety (I) does not have to have a functional group at the terminal thereof. The amphiphilic compound according to the present invention has a hydrocarbon group having 8 or more carbon atoms and a moiety (I) (including a polymer) in the molecule, and when the polymer constituting the moiety (I) has a functional group at the terminal thereof, the functional group may be present at only one terminal of the polymer or at both terminals. Further, the functional group present at the terminal of the polymer may be located on the side where the moiety (I) is bonded to a predetermined hydrocarbon group described later, and may be located on the opposite side.

As the functional group that the polymer constituting the moiety (I) can have, an anionic functional group, a cationic functional group, a nonionic functional group, and an amphoteric functional group are preferable. The functional group is preferably a reactive functional group. Examples of the suitable reactive functional group include a —SH group, a group represented by the formula: —COOM (M represents a hydrogen atom or an alkali metal atom), a hydroxyl group, an allyl group, an epoxy group, an aldehyde group, a —NH$_2$ group, a CONH— group, and the like. Examples of the M include alkali metal atoms such as sodium atom and potassium atom. When the polymer has a functional group at the terminal thereof, the number of the functional groups is not particularly limited, and is preferably 1 to 6, more preferably 1 to 4, and still more preferably 1 to 2.

In order to introduce a functional group into the terminal of the polymer constituting the moiety (I), a functional group-containing compound for introducing a functional group into the polymer can be used. Examples of the functional group-containing compound for introducing a functional group at the terminal of the polymer include thiol chain transfer agents such as alkali metal salts of thioacetic acid, such as sodium thioacetate and potassium thioacetate, cysteine, cysteamine, mercaptoethanol, thioglycerol, thioglycolic acid, mercaptopropionic acid, 2-mercaptopropionic acid, 3-mercaptopropionic acid, thioacetic acid, thiomalic acid, 2-mercaptoethanesulfonic acid, sodium salts and potassium salts thereof; and polymerization initiators with introduced functional groups such as 4,4'-azobis(4-cyanopentanoic acid), 2,2'-azobis[2-methyl-N-[1,1-bis(hydroxymethyl)-2-hydroxyethyl] propionamide], 2,2'-azobis [N-(2-hydroxyethyl)-2-methoxypropanamide], 2,2'-azobis (2-methyl-2-propenylpropanamide), 2,2'-bis(2-imidazolin-2-yl) [2,2'-azobispropane] dihydrochloride, 2,2'-azobis (propane-2-carboamidine) dihydrochloride, 2,2'-azobis[N-(2-carboxyethyl)-2-methylpropion amidin], 2,2'-azobis[2-[1-(2-hydroxyethyl)-2-imidazolin-2-yl] propane cyclohexanone peroxide, acetylacetone peroxide, and the like. These functional group-containing compounds may be used alone, or two or more kinds thereof may be used in combination. The above-mentioned functional group-containing compound include those corresponding to the above-mentioned chain transfer agents and polymerization initiators, but the functional group-containing compounds corresponding to the above-mentioned chain transfer agents and polymerization initiators may be used for the purpose of only one of the chain transfer agent the polymerization initiator and the functional group-containing compound, or may be used for both purposes.

When a living polymerization initiator is used as a polymerization initiator, a functional group may be introduced at the terminal of the polymer by reacting a functional group-containing compound with a halogen atom present at the terminal of the polymer prepared by using the living polymerization initiator. Examples of the functional group-containing compound capable of reacting with such a halogen atom to introduce a functional group at the terminal of the polymer include amine compounds such as ethylenediamine and propyldiamine, dithiol compounds such as ethanedithiol, propanedithiol, and hexadecanedithiol, thiol compounds such as, including allyl mercaptone, cysteine, cysteamine, mercaptoethanol, thioglycerol, thioglycolic acid, mercaptopropionic acid, 2-mercaptopropionic acid, 3-mercaptopropionic acid, thioacetic acid, thiomalic acid, mercaptoethanesulfonic acid, sodium salts and potassium salts thereof, and the like.

The amount of the functional group-containing compound for introducing a functional group into the terminal of the polymer may be set as appropriate according to the type of the monomer (constitutional unit) constituting the polymer, the polymerization conditions such as the polymerization temperature, the target molecular weight of the polymer, and the like, and is not particularly limited. In a case of obtaining a polymer having a number average molecular weight of several thousand to tens of thousands, the amount of the chain transfer agent is preferably 0.1 to 20 parts by mass, and more preferably 0.5 to 15 parts by mass per 100 parts by mass of the monomer.

Examples of the method for introducing a functional group at the terminal of the polymer constituting the moiety (I) include (1) a method for obtaining a polymer by polymerizing a monomer composition in the presence or a polymerization initiator into which the functional group has been introduced as a polymerization initiator, (2) a method for obtaining a polymer by polymerizing a monomer composition in the presence of a chain transfer agent into which the functional group has been introduced as a chain transfer agent, and (3) a method for reacting a halogen atom present at a terminal of a polymer with a functional group-containing compound, and the like, however, the present invention is not limited to such examples.

(Hydrocarbon Group)

The amphiphilic compound according to the present invention also has a hydrocarbon group having 8 or more carbon atoms in addition to the above-mentioned "moiety (I) including a constitutional unit (A) derived from a monomer (a) having two or more hydroxyl groups in the molecule". The specific configuration of the hydrocarbon group is not particularly limited.

As one example, the hydrocarbon group is preferably a group contained in an organic compound having the ability to form an aggregate of molecules by hydrophobic interaction in an aqueous solution. Examples of such organic compounds include hydrocarbons, hydrophobic polymers, lipids, and other organic molecules.

Examples of the hydrocarbons include an aliphatic hydrocarbon having 8 to 50 carbon atoms and an aromatic hydrocarbon having 8 to 50 carbon atoms. That is, in a preferable embodiment of the present invention, the hydrocarbon group has 8 to 50 carbon atoms, more preferably 8 to 40, still more preferably 8 to 30, and particularly preferably 8 to 20.

Examples of the aliphatic hydrocarbons having 8 to 50 carbon atoms include linear alkanes such as octane, nonan, decane, undecane, dodecane, tridecane, tetradecane, pentadecane, hexadecane, heptadecane, octadecane, nonadecane, icosan, branched alkanes thereof, cyclic alkanes thereof, and the like, and linear alkanes are preferable.

Examples of the aromatic hydrocarbons having 8 to 50 carbon atoms include 2-phenylethane, 1,3,5-trimethylbenzene, naphthalene, anthracene, fluorescein, positional isomers thereof, and the like.

Examples of the hydrophobic polymers include polymers obtained by polymerizing a vinyl monomer having a hydrocarbon group having 8 or more carbon atoms in a side chain as a main component among vinyl monomers which can be a constitutional unit of the above-mentioned moiety (I).

The "lipid" means an organic compound having a long-chain fatty acid or a hydrocarbon chain, which is sparingly soluble in water and easily soluble in an organic solvent.

"Lipid" can be further broadly classified into phospholipid, glycolipid, sphingolipid, sterols, neutral lipid, saturated or unsaturated fatty acid, and the like.

Phospholipid is roughly classified into glycerophospholipids and sphingophospholipids. Typical glycerophospholipids include phosphatidylcholine (PC), phosphatidylserine (PS), phosphatidylinositol (PI); phosphatidylgylcerol (PG), phosphatidylethanolamine (PE), and phosphatidylate (PA). On the other hand, a typical sphingophospholipid is sphingomyelin. Specific examples of the phospholipid include the lipids described in (a) to (i) below.

(a) Phosphatidylcholines

Specific examples of phosphatidylcholine species include dipalmitoylphosphatidylcholine (DPPC), distearoylphosphatidylcholine (DSPC), dimyristoylphosphatidylcholine (DMPC), dioleoylphosphatidylcholine (DOPC), dilauroylphosphatidylcholine (DLPC), didecanoylphosphatidylcholine (DDPC), dioctanoylphosphatidylcholine (DOPC), dihexanoylphosphatidylcholine (DHPC), dibutyrylphosphatidylcholine (DBPC), dielaidoylphosphatidylcholine, dilinoleoylphosphatidylcholine, diarachidonoylphosphatidylcholine, dierucoylphosphatidylcholine (DEPC), diheptanoylphosphatidylcholine, dicaproylphosphatidylcholine, diheptadecanoylphosphatidylcholine, dibehenoylphosphatidylcholine, eleostearoylphosphatidylcholine, hydrogenated egg phosphatidylcholine (HEPC), hydrogenated soybean phosphatidylcholine (HSPC), 1-palmitoyl-2-arachidonylphosphatidylcholine, 1-palmitoyl-2-oleoylphosphatidylcholine, 1-palmitoyl-2-linoleoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, 1,2-dimyristoylamide-1,2-deoxyphosphatidylcholine, 1-myristoyl-2-palmitoylphosphatidylcholine, 1-myristoyl-2-stearoylphosphatidylcholine, di-0-hexadecylphosphatidylcholine, transdielideoylphosphatidylcholine, dipalmiterideyl-phosphatidylcholine, n-octadecyl-2-methylphosphatidylcholine, n-octadecylphosphatidylcholine, 1-lauryl propanediol-3-phosphocholine, erythro-N-Lignoceroylsphingo phosphatidycholine, palmitoyl-(9-cis-octadecenoyl)-3-sn-phosphatidylcholine, and the like.

(b) Phosphatidylserines

Specific examples of phosphatidylserines include distearoylphosphatidylserine (DSPS), dimyristoylphosphatidylserine (DMPS), dilauroylphosphatidylserine (DLPS), dipalmitoylphosphatidylserine (DPPS), dioleoylphosphatidylserine (DOPS), lysophosphatidylserine, eleostearoylphosphatidylserine, 1,2-di-(9-cis-octadecenoyl)-3-sn-phosphatidylserine, and the like.

(c) Phosphatidylinositols

Specific examples of phosphatidylinositols include dipalmitoylphosphatidylinositol (DPPI), distearoylphosphatidylinositol (DSPI), dilauroylphosphatidylinositol (DLPI), and the like.

(d) Phosphatidylglycerols

Specific examples of the phosphatidylglycerols include dipalmitylphosphatidylglycerol (DPPG), distearoylphosphatidylglycerol (DSPG), dioleoylphosphatidylglycerol (DOPG), dilauroylphosphatidylglycerol (DLPG), dimyristoylphosphatidylglycerol (DMPG), lysophosphatidylglycerol, hydrogenated soybean glycerol (HSPG), hydrogenated egg phosphatidylglycerol (HEPG), cardiolipin (diphosphatidylglycerol), and the like.

(e) Phosphatidylethanolamines (Cephalin)

Specific examples of phosphatidylethanolamines (cephalin) include dipalmitylphosphatidylethanolamine (DPPE), distearoylphosphatidylethanolamine (DSPE), dioleoylphosphatidylethanolamine (DOPE), dilauroylphosphatidylethanolamine (DLPE), dimyristylphosphatidylethanolamine (DMPE), didecanoylphosphatidylethanolamine (DDPE), N-glutarylphosphatidylethanolamine (NGPE), lysophosphatidylethanolamine, N-(7-nitro-2,1,3-benzoxydiazol-4-yl)-1,2-dioleoyl-sn-phosphatidylethanolamine, eleostearoylphosphatidylethanolamine, N-succinyl dioleoylphosphatidylethanolamine, 1-hexadecyl-2-palmitylglycerophosphatidylethanolamine, and the like. In Production Example 7 described later, distearoyl N-(3-maleimide-1-oxopropyl)-L-α-phosphatidylethanolamine (available from NOF CORPORATION, COAT SOME (Registered Trademark) FE-8080MA3), which is a derivative of distearoylphosphatidylethanolamine (DSPE) having a maleimide group, is used as a raw material for lipids. As described above, phosphatidylethanolamines (and other lipid derivatives) having a functional group such as a maleimide group or a succinimide group for linking with the moiety (I) together with a hydrocarbon group having 8 or more carbon atoms can also be used in the same way.

(f) Phosphatidic Acids

Specific examples of phosphatidic acids include dipalmitoylphosphatidic acid (DPPA), distearoylphosphatidic acid (DSPA), dimyristylphosphatidic acid (DMPA), dioleoylphosphatidic acid (DOPA), and the like.

(g) Sphingophospholipid

Specific examples of sphingophospholipid include sphingomyelin, dipalmitoyl sphingomyelin, distearoyl sphingomyelin, ceramide ciliatine, ceramide phosphorylethanolamine, ceramide phosphorylglycerol and the like.

Glycolipid is roughly classified into glyceroglycolipid and glycosphingolipid. Examples of the glycolipid include the lipids described in (a) to (c) below.

(a) Glyceroglycolipid

Specific examples of the glyceroglycolipid include diglycosyl diglyceride, glycosyl diglyceride, digalactosyl diglyceride, galactosyl diglyceride, sulfoxyribosyl diglyceride, (1,3)-D-mannosyl (1,3) diglyceride, digalactosylglyceride, digalactosyl dilauroylglyceride, digalactosyl dimyristoylglyceride, digalactosyl dipalmitoylglyceride, digalactosyl distearoylglyceride, galactosylglyceride, galactosyl dilauroylglyceride, galactosyl dimyristoylglyceride, galactosyldipalmitoytglyceride, galactosyl distearoylglyceride, digalactosyldiacylglycerol, and the like.

(b) Glycosphingolipid

Specific examples of the glycosphingolipid include ceramide (cerebroside), galactosylceramide, lactosylceramide, digalactosylceramide, ganglioside GM1, ganglioside GM2, ganglioside GM3, sulfatide, ceramide oligohexoside, and globoside.

(c) Other Glycolipids

Examples of other glycolipids include ceramide oligohexoside, palmityl glycoside, stearyl glucoside, myristyl glucoside, alkyl Glycoside, aminophenyl glycoside, cholesteryl maltoside, cholesteryl glucoside, 3-cholesteryl-6'-(glycosylthio) hexyl ether glycolipid, glucosides, and the like.

The most representative of sterols is cholesterol. In addition to cholesterol, sterols include, for example, cholesterol succinic acid, dihydrocholesterol, lanosterol, dihydrolanosterol, desmosterol, stigmasterol, citosterol, campesterol, brush casterol, thymosterol, ergosterol, campersterol, fucosterol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, epicholesterol, dehydroergosterol, cholesterol sulfate, cholesterol hemichoactate, cholesterol phthalate, cholesterol phosphate, cholesterol valerate, cholesterol hemisuccinate, 3βN-(N',N'-dimethylaminoethane)-carbamoyl cholesterol, cholesterol acetate, cholesteryl oleate, cholesteryl linoleate, cholesteryl millistate, cholesteryl palmitate, cholesteryl arachidate, coprostanol, cholesterol ester, cholesteryl phosphorylcholine, 3,6,9-trioxaoctane-1-ol-cholesteryl-3e-ol, and the like.

Examples of the neutral lipid include diglyceride (such as diolein and dipalmitin) and mixed capriline-caprindiglyceride, triacylglycerol (triolein, tripalmitin, trimyristin, trilaurin, tricaprine, tricapriline, tricaproin, and the like), squalene, tocopherol, and cholesterol.

Examples the saturated fatty acid and unsaturated fatty acid include saturated or unsaturated fatty acids having 5 to 30 carbon atoms such as capric acid, pelarganoic acid, capric acid, undecylenic acid, lauric acid, tridecylenic acid, myristic acid, pentadecylenic acid, palmitic acid, margaric acid, stearic acid, nonadecylenic acid, arachidic acid, dodecenoic acid, tetradecenoic acid, oleic acid, linoleic acid, linoleic acid, eicosenoic acid, erucic acid, and docosapentaenoic acid.

For other organic molecules (regardless of natural compounds or chemically synthesized compounds), if they have a hydrocarbon group having 8 or more carbon atoms, the amphiphilic compound according to the present invention can be used as a source of a hydrocarbon group having 8 or more carbon atoms. For example, fat-soluble vitamins such as vitamin A (retinol), vitamin D (calciferol), vitamin E (tocopherol), vitamin K, and derivatives thereof can be mentioned. In addition, the organic molecules consisting of one or more long-chain alkyl chains (8 or more carbon atoms) (for example, dialkylglycerol) and carbon molecules such as fullerene C60 can also be used as a source of hydrocarbon groups having 8 or more carbon atoms.

Here, in a preferable embodiment of the present invention, a hydrocarbon group having 8 or more carbon atoms (preferably having 8 to 50 carbon atoms) is preferably bonded to a moiety (I) including a constitutional unit (A) directly or via a divalent bonding group, or preferably present as a portion of lipids (for example, phospholipids) bonded to the moiety (I) including a constitutional unit (A) directly or via a divalent bonding group.

A hydrocarbon group having 8 or more carbon atoms may also have a functional group at the terminal thereof, similar to the polymer constituting the moiety (I). When a hydrocarbon group having 8 or more carbon atoms has a functional group at the terminal thereof, it becomes possible to modify a medicine or the like via the functional group. However, a hydrocarbon group having 8 or more carbon atoms does not have to have a functional group at the terminal thereof. When a hydrocarbon group having 8 or more carbon atoms has a functional group at the terminal thereof, the functional group may be present only at one terminal of the hydrocarbon group having 8 or more carbon atoms, or may be present at both terminals. Further, the functional group present at the terminal of the hydrocarbon group having 8 or more carbon atoms may be located on the side where the hydrocarbon group having 8 or more carbon atoms is bonded to the moiety (I), or may be located on the opposite side.

The molecular weight of the hydrocarbon group having 8 or more carbon atoms is preferably 5000 or less, preferably 2000 or less, and more preferably 1000 or less from the viewpoint of extracorporeal excretion or the like. It is preferably 100 or more, and more preferably 150 or more. Here, the proportion of the molecular weight of the "hydrocarbon group having 8 or more carbon atoms" to the molecular weight of the amphiphilic compound is preferably 0.2 to 20%, more preferably 0.5 to 15%, and still more preferably 1 to 10%.

Further, in the present invention, when a hydrocarbon group having 8 or more carbon atoms is present in the amphiphilic compound as a part of the lipid, the molecular weight of the lipid is preferably 2000 or less, and more preferably 1000 or less. Here, when a hydrocarbon group having 8 or more carbon atoms is present in the amphiphilic compound as a part of the lipid, the proportion of the molecular weight of the lipid to the molecular weight of the amphiphilic compound is preferably 2 to 50%, more preferably 5 to 35%, and still more preferably 10 to 20%.

The divalent bonding group is a group that bonds a moiety (I) and a hydrocarbon group having 8 or more carbon atoms, and the structure is not particularly limited and may be included in a portion of the structure of the moiety (I). Specifically, as such a divalent bonding group, —S—, —S—C(=S)—, —S—C(=S)—S—, —S—C(=S)—N(—$R_a$)—, —S—C(=S)—O—, —S—$R_b$—C(=O)—O—, —S—$R_b$—C(=O)—N(—$R_a$)—, —S—$R_b$—O—, —S—$R_b$—O—C(=O)—, —O—, —O—C(=O)—, —N(—$R_a$)—C(=O)— and divalent bonding groups containing these are exemplified. Here, the above $R_a$ is a hydrogen atom or a hydrocarbon group having 1 to 30 carbon atoms. The above $R_b$ is a hydrocarbon group having 1 to 30 carbon atoms. The residue obtained by removing one hydrogen atom and one hydrocarbon group having 8 or more carbon atoms from the lipids (including a modified product of the lipid) is also one of the preferable forms of the divalent bonding group. The molecular weight of the divalent bonding group is preferably 5000 or less, more preferably 2000 or less, and still more preferably 1000 or less.

Here, examples of the method for linking a hydrocarbon group having 8 or more carbon atoms and the moiety (I) via a divalent bonding group include a method of using a chain transfer agent or a polymerization initiator having a structure in the molecule that can form a moiety containing a hydrocarbon group having 8 or more carbon atoms, as the chain transfer agent and/or the polymerization initiator, when the monomer composition is polymerized in the presence of the chain transfer agent and/or the polymerization initiator to obtain a polymer constituting the moiety (I). In particular, by polymerizing a monomer composition using the chain transfer agent having a thiol group (—SH group) bonded to a hydrocarbon group having 8 or more carbon atoms, an amphiphilic compound in which a hydrocarbon group having 8 or more carbon atoms is bonded to the moiety (I) via a thioether bond (—S—) can be obtained (refer to Production Examples 1 to 6 described later).

In addition, as another method for linking a hydrocarbon group having 8 or more carbon atoms and the moiety (I) via a divalent bonding group, a thiol group (—SH group) is introduced at the terminal of the polymer constituting the moiety (I) by performing RAFT polymerization using a reversible additional cleavage chain transfer (RAFT) agent as the chain transfer agent, when the monomer composition is polymerized in the presence of the chain transfer agent to obtain a polymer constituting the moiety (I). Subsequently, a compound having a functional group (for example, a maleimide group or the like) capable of reacting with a thiol group (—SH group) is reacted with the thiol group (—SH group) together with a hydrocarbon group having 8 or more carbon atoms. With this, the hydrocarbon group having 8 or more carbon atoms and the moiety (I) can be linked via the thioether bond (—S—) (refer to Production Example 7 described later). This technique is particularly useful when the hydrocarbon group with 8 or more carbon atoms is present in the amphiphilic compound as a portion of lipids or other organic molecules.

In the amphiphilic compound according to the present invention, the polymer constituting the moiety (I) or the polymer in which a hydrocarbon group having 8 or more carbon atoms is present in the compound as a portion of the polymer may have a crosslinked structure. Examples of the method for cross-linking the polymer include a chemical cross-linking method, a physical cross-linking method, and the like. Examples of the chemical cross-linking method include a method for cross-linking the polymer with a chemical cross-linking agent such as an epoxy compound, an oxidized starch, glutaaldehyde, formaldehyde, dimethyl suberiminoate, carbodiimide, a succinimidyl compound, a diisosianato compound, acyl aside, reuterin, tris(hydroxymethyl) phosphine, copper ascorbate, glucose lysine, or a photooxidant, a method of chemically cross-linking a polymer by, for example, heat dehydration treatment, irradiation with ultraviolet rays, irradiation with electron beams, irradiation with gamma rays, and the like. Examples of the physical cross-linking method include a method for cross-linking a polymer with a salt, a method for cross-linking a polymer by electrostatic interaction, a method for cross-linking a polymer with hydrogen bonding, a method for cross-linking a polymer by hydrophobic interaction, and the like. The cross-linking methods may be also used alone, or two or more kinds thereof may be used in combination.

The number average molecular weight (Mn) of the amphiphilic compound according to the present invention is preferably 1000 or more, more preferably 2000 or more, and preferably 100000 or less and more preferably 50000 or less.

Application of Amphiphilic Compound

Since the amphiphilic compound according to the present invention has high biocompatibility, it can be suitably used for medical applications. That is, according to another aspect of the present invention, there is provided a medical resin composition containing an amphiphilic compound according to the present invention. This medical resin composition may consist of the amphiphilic compound according to the present invention, or may further contain other components. Examples of other components include water, saline, a pharmaceutically acceptable organic solvent, collagen, polyvinyl alcohol, polyvinylpyrrolidone, a carboxyvinyl polymer, a sodium carboxymethyl cellulose salt, sodium polyacrylate, sodium alginate, water-soluble dextran, sodium carboxymethyl starch, pectin, methyl cellulose, ethyl cellulose, xanthan gum, gum arabic, casein, gelatin, agar, diglycerin, propylene glycol, polyethylene glycol, petrolatum, paraffin, stearyl alcohol, stearic acid, human serum albumin, mannitol, sorbitol, lactose, phosphate buffered saline, a biodegradable polymer, serum-free medium, a surfactant acceptable as a pharmaceutical additive, a physiological pH buffer acceptable in vivo, and the like. These additives may be used alone, or two or more kinds thereof may be used in combination.

The amphiphilic compound or medical resin composition according to the present invention can be suitably used as a pharmaceutical additive. Examples of the pharmaceutical additive include a carrier for holding a medicine and the like. Examples of the method for holding a medicine or the like with the amphiphilic compound or the medical resin composition according to the present invention include a method for compounding a carrier, a medicine, or the like by bonding a medicine or the like to a moiety (I) constituting an amphiphilic compound or a functional group having a hydrocarbon group having 8 or more carbon atoms, a method for mixing an amphiphilic compound or a medical resin composition with a medicine or the like so as to have a uniform composition, a method for a coating particle of a medicine or the like with an amphiphilic compound or a medical resin composition, a method for converting a mixture of a lipid and an amphiphilic compound or a medical resin composition into particles, and encapsulating the medicine or the like inside the obtained particles, a method for encapsulating a particle inside the outer skin of an amphiphilic compound or a medical resin composition by coating the particle encapsulating a medicine or the like in a liposome with the amphiphilic compound or the medical resin composition, a method for encapsulating a particle inside the outer skin of an amphiphilic compound or a medical resin composition by coating the particle of a mixture of a medicine or the like and a liposome with the amphiphilic compound or the medical resin composition, a method for encapsulating a medicine or the like by micellarizing the medicine or the like with an amphiphilic compound or a medical resin composition, a method for encapsulating a medicine or the like by making the medicine or the like into a liposome with an amphiphilic compound and a lipid constituting a liposome, and the like. However, the present invention is not limited to such examples.

The liposome was prepared by, for example, a method for dissolving the lipid in a solvent such as tert-butyl alcohol and then freeze-drying, or adding a solution in which the drug was dissolved to the lipid to swell the lipid and disperse it with ultrasonic waves, and then, adding polyethylene glycol-phosphatidylethanolamine or the like to the obtained dispersion.

The liposome is preferably cationized with a cationizing agent. As the cationizing agent, ones known in the related art can be appropriately selected and used. The liposome can be obtained, for example, by dissolving hydrogenated soybean lecithin, cholesterol, 3,5-dipentadecyloxybenzamidine hydrochloride, and the like in a solvent such as tert-butyl alcohol, and freezing the obtained lipid mixed solution. The lipid that makes up a liposome is stable in vivo. As the lipid, those exemplified above as a source of a hydrocarbon group having 8 or more carbon atoms can be used in the same way.

In the above example, the liposome has been mentioned, but instead of the liposome, for example, an emulsion, a nanoparticle, a microparticle, a polymer compound, and the like can be used.

As the medicine, a medicine that is biologically or pharmacologically active can be used. Examples of the medicines include an antitumor agent, an anticancer agent, an antibiotic, an antiviral agent, an anticancer effect enhancer, an immunopotentiator, an immunomodulator, an immunorecovery agent, a radiation sensitizer, a radiation protective agent, an antihistamine agent, an anti-inflammatory agent, a congestion remover, an antifungal agent, an arthritis drug, an anti-asthma drug, an angiogenesis inhibitor, an enzyme drug, an antioxidant, hormone, an angiotensin converting enzyme inhibitor, a smooth muscle cell proliferation agent, a smooth muscle cell migration inhibitor, a platelet aggregation inhibitor, a chemical mediator release inhibitor, a proliferation promoter for a vascular endothelial cell, an inhibitor of vascular endothelial cell growth, interferon, interleukin, a colony stimulating factor, cytokine, a tumor necrosis factor, a granulocyte macrophage colony stimulating factor, a granulocyte colony stimulating factor, a macrophage colony stimulating factor, a stem cell factor, a β-transforming growth factor, a hepatocyte growth factor, a vascular endothelial growth factor, erythropoietin, vaccine, protein, mucoprotein, peptide, polysaccharide, lipopolysaccharide, sugar chain, antisense, ribozyme, decoy, nucleic acid, an antibody, and the like. These medicines may be used alone, or two or more kinds thereof may be used in combination.

Mammals such as humans, monkeys, mice, and livestock are examples of the subject to which the medicine is administered, but the present invention is not limited to these examples.

When the medicine is administered by injection, the medicine can be injected into the body by, for example, intravenous injection such as instillation, intramuscular injection, intraperitoneal injection, subcutaneous injection, intradermal injection, intratumoral injection, or the like. Here, as described above, the hydrophilic moiety of the amphiphilic compound according to the present invention has lower adsorptivity to plastics such as PP as compared with PVP. Therefore, the compound can be applied to long-term blood-retaining liposomes and the like as a drug carrier while reducing the adsorptivity to plastics. As a result, for example, it is possible to reduce the possibility that the active component encapsulated in the liposome modified with the compound remains in the syringe. Therefore, one of the preferable applications of the amphiphilic compound or medical resin composition according to the present invention is a pharmaceutical additive used as a carrier for holding a medicine or the like in the form of a liposome or the like. The pharmaceutical additive is preferably added to the pharmaceutical administered in the form of an injection.

The amount of the medicine to be held in the amphiphilic compound or the medical resin composition according to the present invention varies depending on the subject to which the medicine is administered, the type of the medicine, and the like, and therefore cannot be unconditionally determined. Usually, the amount of the medicine is preferably about 1 µg to 50 g per 100 g of the solid content contained in the amphiphilic compound or the medical resin composition according to the present invention.

EXAMPLES

Hereinafter, the present invention will be described in detail with reference to examples, but the present invention is not limited thereto.

Measurement of Average Molecular Weight of Polymer

The number average molecular weight of the polymers produced in Production Examples 1 to 7 and Comparative Production Example 1 described later was measured by gel permeation chromatography (GPC). At this time, the measurement conditions were as follows.

Measurement Conditions for Number Average Molecular Weight of Polymer (Polymers Obtained in Production Examples 1 to 7)

Measuring equipment: available from Tosoh Corporation, product number: HLC-8320GPC
Molecular weight column: available from Tosoh Corporation, product number: TSKgel SuperAWM-H and SuperAW2500 are connected in series.
Eluent: Dimethylformamide added with 10 mmol/L lithium bromide
Standard material for calibration curve: Polystyrene
Preparation of solution for measurement: A solution in which a polymer is dissolved in dimethylformamide to have a polymer concentration of 0.2% by mass is prepared, and the filtrate after filtering the solution with a filter is used.

Measurement Conditions for Number Average Molecular Weight of Polymer (Polymers Obtained in Comparative Production Example 1)

Measuring equipment: available from Tosoh Corporation, product number: HLC-8320GPC
Molecular weight column: available from Tosoh Corporation, product number: TSKgel α-M and α-2500 are connected in series.
Fluent: A mixed solution of 80 vol % of 0.2 M sodium nitrate aqueous solution and 20 vol % of acetonitrile
Standard material for calibration curve: Polyethylene glycol
Preparation of solution for measurement: A solution in which a polymer is dissolved in the eluent to have a polymer concentration of 0.2% by mass is prepared, and the filtrate after filtering the solution with a filter is used.

Production Example of Amphiphilic Compound (Polymer)

An amphiphilic compound having a polymer form was produced by the following method.

Production Example 1

In a Schlenk flask with a three-way cock, 1.0 g of glycerin monoacrylate, 0.071 g of 4-cyano-4-(dodecylsulfanylthiocarbonyl) sulfanylpentanoate, to 0.022 g of 2,2'-azobis (isobutyronitrile), 1.8 g of ethanol, and 0.2 g of water were charged. Next, nitrogen was substituted inside the flask, and the mixture was stirred at 70° C. for 1 hour. The obtained reaction solution was added dropwise to diethyl ether for purification to obtain polyglycerin monoacrylate containing an alkyl group (n-dodecyl group) at a terminal. The number average molecular weight of the obtained amphiphilic compound (polymer) was 2200. Among these, the molecular weight of the hydrocarbon group (n-dodecyl group) having 8 or more carbon atoms is 169.3.

Production Example 2

In a Schlenk flask with a three-way cock, 1.0 g or glycerin monoacrylate, 0.043 g of 4-cyano-4-(dodecylsulfanylthiocarbonyl) sulfanylpentanoate, 0.013 g of 2,2'-azobis(isobutyronitrile), 1.8 g of ethanol, and 0.2 g of water were charged. Next, nitrogen was substituted inside the flask, and the mixture was stirred at 70° C. for 1 hour. The obtained reaction solution was added dropwise to diethyl ether for purification to obtain polyglycerin monoacrylate containing an alkyl group (n-dodecyl group) at a terminal. The number average molecular weight of the obtained amphiphilic compound (polymer) was 10900. Among these, the molecular weight of the moiety (n-dodecyl group) containing a hydrocarbon group having 8 or more carbon atoms is 169.3.

Production Example 3

In a Schlenk flask with a three-way cock, 1.0 g glycerin monoacrylate, 0.098 g of 1-octadecanethiol, 0.021 g of 2,2'-azobis(isobutyronitrile), 2.25 g of ethanol, and 0.25 g of water were charged. Next, nitrogen was substituted inside the flask, and the mixture was stirred at 80° C. for 3 hours. The obtained reaction solution was added dropwise to diethyl ether for purification to obtain polyglycerin monoacrylate containing an alkyl Group (n-octadecyl group) at a terminal. The number average molecular weight of the obtained amphiphilic compound (polymer) was 4100. Among these, the molecular weight of the hydrocarbon group (n-octadecyl group) having 8 or more carbon atoms is 253.5.

Production Example 4

In a Schlenk flask with a three-way cock, 1.0 g glycerin monoacrylate, 0.049 g of 1-octadecanethiol, 0.014 g of 2,2'-azobis(isobutyronitrile), 1.8 g of ethanol, and 0.2 g of water were charged. Next, nitrogen was substituted inside the flask, and the mixture was stirred at 80° C. for 3 hours. The obtained reaction solution was added dropwise to diethyl ether for purification to obtain polyglycerin monoacrylate containing an alkyl Group (n-octadecyl group) at a terminal. The number average molecular weight of the obtained amphiphilic compound (polymer) was 8600. Among these, the molecular weight of the hydrocarbon group (n-octadecyl group) having 8 or more carbon atoms is 253.5.

Production Example 5

In a Schlenk flask with a three-way cock, 1.0 g of glycerin monomethacrylate, 0.045 g of 1-octadecanethiol, 0.013 g of 2,2'-azobis(isobutyronitrile), 1.6 g ethanol, and 0.4 g of n-butanol were charged. Next, nitrogen was substituted inside the flask, and the mixture was stirred at 80° C. for 3 hours. The solution portion of the obtained reaction solution was added dropwise to diethyl ether for purification to obtain polyglycerin monomethacrylate containing an alkyl group (n-octadecyl group) at a terminal. The number average molecular weight of the obtained amphiphilic compound (polymer) was 4100. Among these, the molecular weight of the hydrocarbon group (n-octadecyl group) having 8 or more carbon atoms is 253.5.

Production Example 6

In a Schlenk flask with a three-way cock, 1.0 g of glycerin monomethacrylate, 0.045 g of 1-octadecanethiol, 0.013 g of 2,2'-azobis(isobutyronitrile), 1.6 g of ethanol, and 0.4 g of n-butanol were charged. Next, nitrogen was substituted inside the flask, and the mixture was stirred at 80° C. for 3 hours. The precipitated portion of the obtained reaction solution was dissolved in 1.0 g of ethanol and further added dropwise to diethyl ether for purification to obtain polyglycerin monomethacrylate containing an alkyl group (n-octadecyl group) at a terminal. The number average molecular weight of the obtained amphiphilic compound (polymer) was 14000. Among these, the molecular weight of the hydrocarbon group (n-octadecyl group) having 8 or more carbon atoms is 253.5.

Production Example 7

In a Schlenk flask with a three-way cock, 1.0 g of glycerin monomethacrylate, 0.022 g of 4-cyano-4-(phenylcarbonothioilthio) pentanoic acid, 0.016 g of 2,2'-azobis(2,4-dimethylvaleronitrile), 0.8 g of ethanol, and 0.2 g of n-butanol were charged. Next, nitrogen was substituted inside the flask, and the mixture was stirred at 50° C. for 30 minutes. The obtained reaction solution was added dropwise to diethyl ether for purification. 0.2 g of the obtained polymer, 0.25 g of propylamine, and 1.0 g of water were charged, stirred overnight at room temperature, and freeze-dried to obtain polyglycerin monomethacrylate having a thiol group introduced at the terminal. The number average molecular weight of the obtained polymer was 5200.

Then, in a 10 mL screw tube, 0.0165 g of the polymer obtained above, 0.0276 g of distearoyl N-(3-maleimide-1-oxopropyl)-L-α-phosphatidylethanolamine (available from NOF CORPORATION, COAT SOME Trademark) FE-8080MA3), 75 μL of triethylamine, 0.06 g of chloroform, and 0.4 g of methanol were charged. Then, after reacting overnight at room temperature, the mixture was added dropwise to diethyl ether for purification to obtain polyglycerin monomethacrylate containing a lipid at the terminal. The number average molecular weight of the obtained amphiphilic compound (polymer) was 6000. Among these, the molecular weight of a lipid portion, which is a source of hydrocarbon group having 8 or more carbon atoms, is about 954.

Comparative Production Example 1

In a Schlenk flask with a three-way cock, 1.0 g of N-vinyl-2-pyrrolidone, 0.064 g of octadecanethiol, 0.018 g of 2,2'-azobis(isobutyronitrile), 1.6 g of ethanol, and 0.4 g of n-butanol were charged. Next, nitrogen was substituted inside the flask, and the mixture was stirred at 80° C. for 3 hours. The obtained reaction solution was added dropwise to diethyl ether for purification to obtain polyvinylpyrrolidone containing an alkyl group (n-octadecyl group) at a terminal. The number average molecular weight of the obtained amphiphilic compound (polymer) was 12000. Among these, the molecular weight of the hydrocarbon group (n-octadecyl group) having 8 or more carbon atoms is 253.5.

Preparation of Liposome 17.6 mg of hydrogenated soybean-derived phosphatidylcholine (Avanti Polar Lipids) and 4.7 mg of cholesterol (Tokyo Chemical industry Co., Ltd.) were dissolved in 20 mL of methanol, charged in a 200 mL of eggplant flask, and evaporated in a water bath at 65° C. to form a lipid membrane. 3 mL of PBS containing 20 w/v % glucose was added thereto, and the mixture was sealed and warm-bathed at 65° C. for 30 minutes to be hydrated to prepare a lipid suspension. The lipid suspension was transferred to a microtest tube, 4 times the amount of PBS was added, and then centrifuged at 15000×G for 20 minutes to precipitate the formed liposomes. After centrifugation, a mixture obtained by discarding a supernatant, and adding 1 mL of new PBS and resuspending was sized with an extruder (pore size 0.1 μm) warmed to 65° C. to obtain a liposome suspension having a lipid equivalent of 12.9 mg/mL. The concentration of the liposome suspension was measured using Lab Assay (trademark) phospholipid (FUJIFILM Wako Pure Chemical Corporation), and the measurement protocol was based on the attached manual.

Modification of Amphiphilic Compound (Polymer) on Liposome

Figure 1:
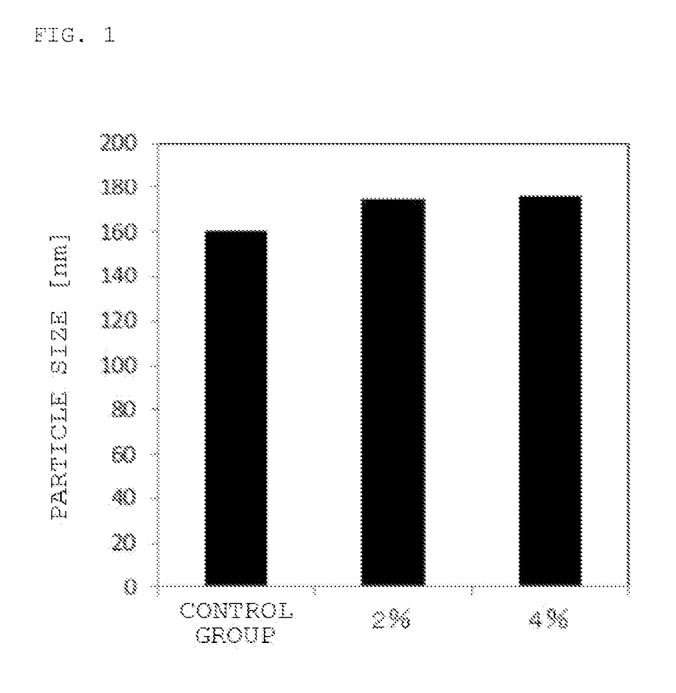
FIG. 1 is a graph illustrating a particle size of liposomes modified with an amphiphilic compound (polymer) (2 w/v % or 4 w/v % PBS solution) prepared in Production Example 4 in comparison with that of unmodified liposomes.

Polyglycerin monoacrylate (number average molecular weight 8600) containing an alkyl group (n-octadecyl group)

at the terminal, which is an amphiphilic compound (polymer) prepared in the above Production Example 4 was dissolved in PBS to be a concentration of 2 w/v % or 4 w/v % to prepare a polymer solution having different concentrations. Each of the polymer solutions and the liposome suspension prepared above were mixed in equal volumes and allowed to stand at 10° C. for 60 minutes to modify the amphiphilic compound into liposomes. Here, it is presumed that by inserting the alkyl group portion of the terminal alkyl group-containing polymer into the lipid bilayer membrane constituting the liposome, a structure in which the surface of the liposome is modified (coated) by the hydrophilic moiety of the polymer is obtained. On the other hand, a control group was prepared by mixing and reacting the same volume of PBS instead of the polymer solution. Then, the mixture was centrifuged at 15000×G for 20 minutes, the supernatant was removed to remove the unreacted amphiphilic compound, and the formed precipitate was resuspended in PBS. The particle size of each liposome was measured with Zetasizer Nano ZS (Malvern Panalytical). As a result, as illustrated in FIG. 1, the particle size of the liposome was 160.6±5.2 nm in the control group. In contrast, it was confirmed that the particle sizes of liposomes modified with 2 w/v % and 4 w/v % polymer solutions were 174.8±6.5 nm and 174.6±5.5 nm, respectively, and the particle size was increased by modification with using the amphiphilic compound.

Cytotoxicity Test of Amphiphilic Compound (Polymer) Using Cultured Cells

L929 cells (DS Pharma Biomedical), which are mouse-derived fibroblasts, were cultured in DMEM medium (Nacalai Tesque) supplemented with fetal bovine serum (FBS) (DS Pharma Biomedical) at a final concentration of 10 w/v %. The cells were seeded on a 100 mm cell culture dish (BD Falcon) so as to have a size of $5.0 \times 10^3$ cells/cm$^2$, and cultured under 37° C. and 5% $CO_2$ conditions. L929 cells cultured in a 100 mm cell culture dish to a 70% confluent state were treated with 0.25 w/v % trypsin/50 mM EDTA solution, and the above-mentioned serum-added DMEM medium was added to stop the trypsin reaction to obtain an L929 cell suspension. The number of cells in the L929 cell suspension was measured using a 0.4 w/v % trypan blue solution (FUJIFILM Wako Pure Chemical Corporation). The cell suspension was seeded on a 96-well plate (Thermo Fisher Science) so that the number of cells per well was $2.5 \times 10^3$ cells, and cultured for 24 hours under 37° C. and 5% $CO_2$ conditions. After 24 hours, 50 μL of the medium was removed from each well, 50 μL of a polymer solution in which amphiphilic compounds (polymers) prepared in Production Examples 1 to 7 and Comparative Production Example 1 were dissolved in PBS to 2 w/v % was added to each well, and the mixture was incubated at 37° C. for 24 hours under 5% $CO_2$ conditions. After incubation, 51 μL of Cell Growth Kit II (XTT) (Sigma-Aldrich) reagent was added to each well, and the cells were incubated at 37° C. for 3 hours under 5% $CO_2$ conditions. Then, the absorbance was measured with a plate reader SH-9000 (Corona Electric Co., Ltd.). The measurement protocol conformed to the manual attached to the kit. The survival rate of L929 cells was calculated from the following formula based on the measured values of the wells tested by adding PBS instead of the polymer solution and the measured values of the wells to which each sample was added.

(Survival rate)[%]=(Measured value of well with each sample added)/(Measured value of well with PBS added)×100

Figure 2:
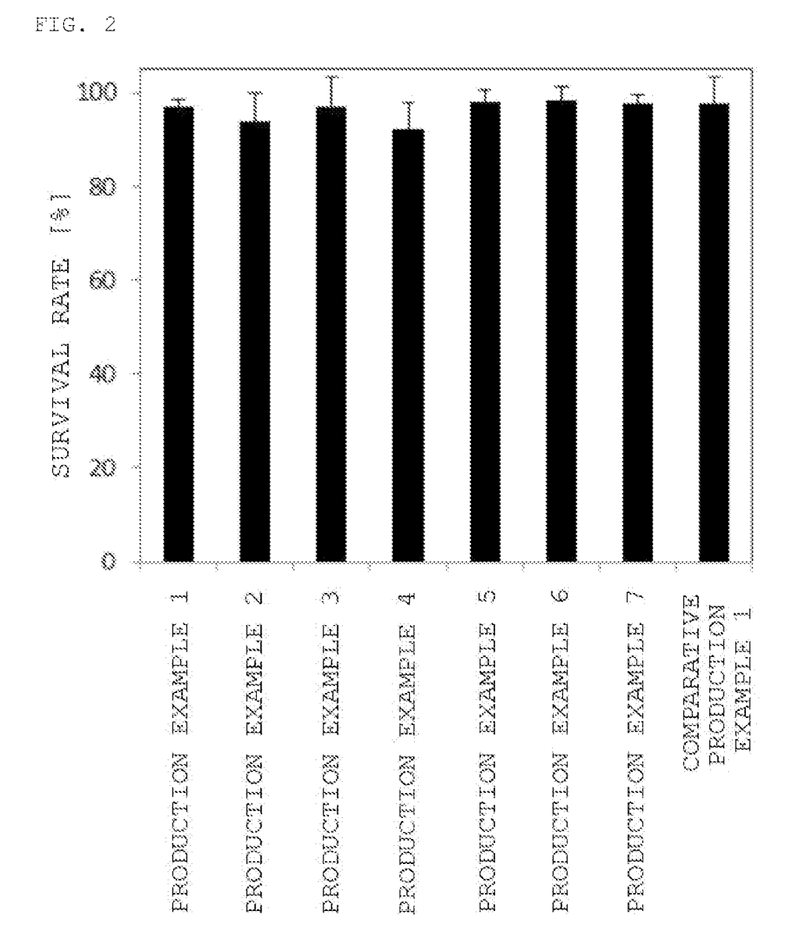
FIG. 2 is a graph illustrating a cell survival rate of mouse-derived fibroblasts (L929 cells) cultured in the presence of a 2 w/v % PBS solution of the amphiphilic compounds (polymers) prepared in Production Examples 1 to 7 and Comparative Production Example 1.

As a result, as illustrated in FIG. 2, none of the polymer solutions gave a significant difference in the survival rate of L929 cells, and no significant cytotoxicity was observed.

Cytotoxicity Test of Amphiphilic Compound (Polymer)-Modified Liposomes Using Cultured Cells L929 cells (DS Pharma Biomedical), which are mouse-derived fibroblasts, were cultured in DMEM medium (Nacalai Tesque) supplemented with fetal bovine serum (FBS) (DS Pharma Biomedical) at a final concentration of 10 w/v %. The cells were seeded on a 100 mm cell culture dish (BD Falcon) so as to have a size of $5.0 \times 10^3$ cells/cm$^2$, and cultured under 37° C. and 5% $CO_2$ conditions. L929 cells cultured in a 100 mm cell culture dish to a 70% confluent state were treated with 0.25 w/v % trypsin/50 mM EDTA solution, and the above-mentioned serum-added DMEM medium was added to stop the trypsin reaction to obtain an L929 cell suspension. The number of cells in the L929 cell suspension was measured using a 0.4 w/v % trypan blue solution (FUJIFILM Wako Pure Chemical Corporation). The cell suspension was seeded on a 96-well plate (Thermo Fisher Science) so that the number of cells per well was $2.5 \times 10^3$ cells, and cultured for 24 hours under 37° C. and 5% $CO_2$ conditions. After 24 hours, 50 μL of medium was removed from each well. Then, according to the description in the section "Modification of amphiphilic compound (polymer) on liposome", 50 μL each of the modified or unmodified liposome suspension (both 5 mg-lipid/mL) obtained using a 2 w/v % solution of the amphiphilic compound (polymer) prepared in Production Examples 1 to 7 and Comparative Production Example 1 described above was added, and incubated for 24 hours under 37° C. under the 5% $CO_2$ conditions. After incubation, 51 μL of Cell Growth Kit II (XTT) (Sigma-Aldrich) reagent was added to each well, and the cells were incubated at 37° C. for 3 hours under 5% $CO_2$ conditions. Then, the absorbance was measured with a plate reader SH-9000 (Corona Electric Co., Ltd.). The measurement protocol conformed to the manual attached to the kit. The survival rate of L929 cells was calculated from the following formula based on the measured values of the wells tested by adding PBS instead of the modified liposome suspension and the measured values of the wells to which each sample was added.

(Survival rate)[%]=(Measured value of well with each sample added)/(Measured value of well with PBS added)×100

Figure 3:
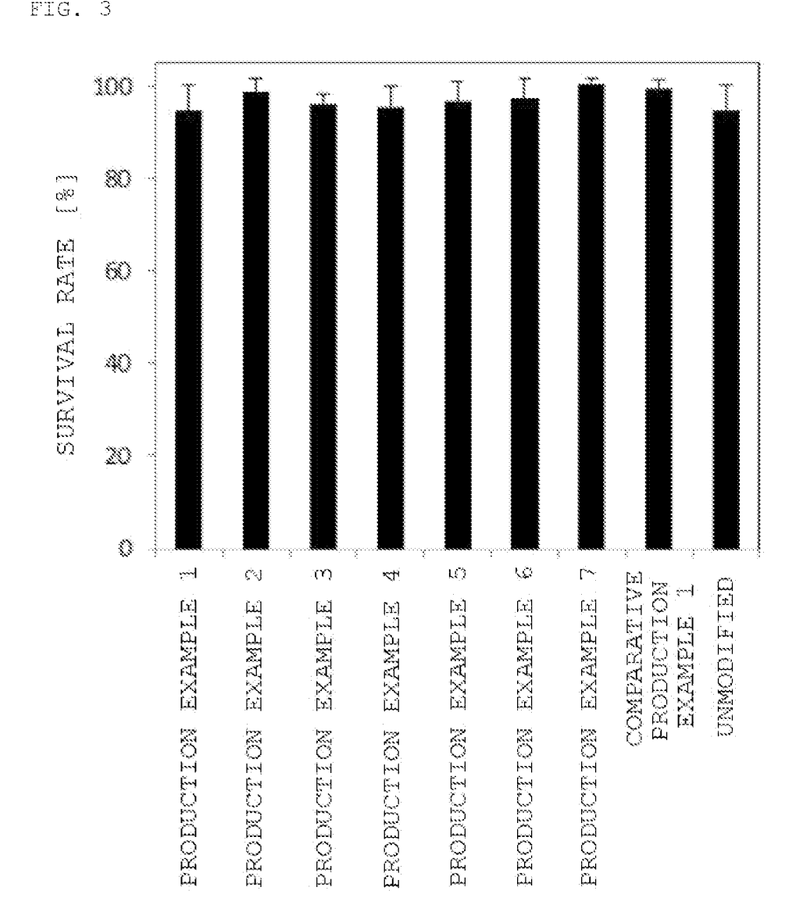
FIG. 3 is a graph illustrating a cell survival rate of mouse-derived fibroblasts (L929 cells) cultured in the presence of liposomes modified with solution the 2 w/v % PBS solution of the amphiphilic compounds (polymers) prepared in Production Examples 1 to 7 and Comparative Production Example 1 in comparison with unmodified liposomes.

As a result, as illustrated in FIG. 3, the liposomes modified with any amphiphilic compound (polymer) did not give a significant difference in the survival rate of L929 cells, and no significant cytotoxicity was observed.

Adsorption Test of Amphiphilic Compound (Polymer) on Plastic Surface

Each of the amphiphilic compounds (polymers) prepared in Production Example 4 and Production Example 6 and Comparative Production Example 1 was dissolved in PBS so as to have a concentration of 1 w/v % to prepare a polymer solution. 4.5 mL of this polymer solution and 1.5 g of polypropylene (PP) fine powder (average particle size of 5 micron meter) were charged in a screw cap bottle and stirred with a stirrer for 30 minutes. After stirring, the polymer concentration of each polymer solution was quantified from a peak area of GPC. From the initial polymer concentration ($C_0$) and the polymer concentration ($C_t$) after the test, the adsorption amount of polymer per 1 g of fine powder was calculated using the following formula. The results are indicated in Table 1.

(Adsorption amount to fine powder)[mg/g]=($C_t$-$C_0$)/ (fine powder [g])

TABLE 1

| Constituent component of moiety (I) | Adsorption amount to fine powder [mg/g] |
|---|---|
| PVP | 6.0 |
| GLMMA | 2.4 |
| GLMA | 1.5 |

As can be seen from the results illustrated in Table 1, as compared with the amphiphilic compound (polymer) having the moiety (I) consisting of PVP, the amphiphilic compound (polymer) having the moiety (I) consisting of GLMMA or GLMA has significantly less adsorption to polypropylene (PP) fine powder.

Preparation of Fluorescent Substance-Encapsulated Liposome 17.6 of hydrogenated soybean-derived phosphatidylcholine (Avanti Polar Lipids) and 4.7 mg of cholesterol (Tokyo Chemical Industry Co., Ltd.) were dissolved in 20 mL of methanol, charged in a 200 mL of eggplant flask, and evaporated in a water bath at 6.5° C. to form a lipid membrane. 3 mL of PBS containing 20 w/v % glucose and 0.02% w/v fluorescein isothiocyanate (FITC) was added thereto, and the mixture was sealed and warm-bathed at 65° C. for 30 minutes to be hydrated to prepare a lipid suspension. The lipid suspension was transferred to a microtest tube, 4 times the amount of PBS was added, and then centrifuged at 15000×G for 20 minutes to precipitate the formed liposomes. After centrifugation, a mixture obtained by discarding a supernatant, and adding 1 mL of new PBS and resuspending was sized with an extruder (pore size 0.1 μm) warmed to 65° C. to obtain a liposome suspension having a lipid equivalent of 13.7 mg/mL. The concentration of the liposome suspension was measured using Lab Assay (trademark) phospholipid (FUJIFILM Wako Pure Chemical Corporation), and the measurement protocol was based on the attached manual.

Preparation of PEG-Modified Liposome 12.9 mg of hydrogenated soybean-derived phosphatidylcholine (Avanti Polar Lipids), 3.4 mg of cholesterol (Tokyo Chemical Industry Co., Ltd.), and 3.76 mg of PEG-phospholipid (available from NOF CORPORATION, SUNBRIGHT (Trademark) DSPE-020CN) were dissolved in 20 mL of methanol, charged in a 200 ml of eggplant flask, and evaporated in a water bath at 65° C. to form a lipid membrane. 3 mL of PBS containing 20 w/v % glucose and 0.02% w/v FITC was added thereto, and the mixture was sealed and warm-bathed at 65° C. for 30 minutes to be hydrated to prepare a lipid suspension. The lipid suspension was transferred to a microtest tube, 4 times the amount of PBS was added, and then centrifuged at 15000×G for 20 minutes to precipitate the formed liposomes. After centrifugation, a mixture obtained by discarding a supernatant, and adding 1 mL of new PBS and resuspending was sized with an extruder (pore size 0.1 μm) warmed to 65° C. to obtain a liposome suspension having a lipid equivalent of 9.7 mg/mL. The concentration of the liposome suspension was measured using Lab Assay (trademark) phospholipid (FUJIFILM Wako Pure Chemical Corporation), and the measurement protocol was based on the attached manual.

Cell Uptake Test of Amphiphilic Compound (Polymer)-Modified Liposomes using Cultured Cells HepG2 cells (DS Pharma Biomedical), which is a human liver cancer-derived cell line, were cultured in MEM medium (Nacalai Tesque) supplemented with fetal bovine serum (FBS) (DS Pharma Biomedical) at a final concentration of 10 w/v %. The cells were seeded on a 100 mm cell culture dish (BD Falcon) so as to have a size of $5.0 \times 10^3$ cells/cm$^2$, and cultured under 37° C. and 5% $CO_2$ conditions. HePG2 cells cultured in a 100 mm cell culture dish to a 70% confluent state were treated with 0.25 w/v % trypsin/ 50 mM EDTA solution, and the above-mentioned serum-added MEM medium was added to stop the trypsin reaction to obtain a HepG2 cell suspension. The number of cells in the HepG2 cell suspension was measured using a 0.4 w/v % trypan blue solution (FUJIFILM Wako Pure Chemical Corporation). The cell suspension was seeded on a 24-well plate (Thermo Fisher Science) so that the number of cells per well was $4 \times 10^4$ cells, and cultured or 48 hours under 37° C. and 5% $CO_2$ conditions. After 48 hours, the medium was removed from each well and 500 μL of MEM medium without serum was added. Then, by using a 2 w/v % solution of the amphiphilic compound (polymer) prepared in Production Example 4 described above, 50 μL each of the fluorescent substance-encapsulated liposome according to the description in the section "Modification of amphiphilic compound (polymer) on liposome", the PEG-modified liposome prepared according to the description in the [Preparation of PEG-modified liposome] section, unmodified liposome suspension (both 5 mg-lipid/mL) was added, and incubated for 3 hours under 37° C. or 4° C. under the 5% $CO_2$ conditions. After incubation, the medium in each well was removed, washed twice with PBS, and then 350 μL of 0.2 mol/L sodium hydroxide aqueous solution containing 0.02 w/v Triton X-100 was added to dissolve the cells to measure the fluorescence intensity of the solution by a plate reader SH-9000 (Corona Electric Co., Ltd.). Based on the measured values of the wells incubated at 4° C. and the wells incubated at 37° C., the amount of uptake of the liposomes into HepG2 cells was calculated from the following formula.

(Uptake)[–]=(Measured value of wells incubated at 37° C.)–(Measured value of wells incubated at 4° C.)

Next, the ratio of the uptake amount to the unmodified liposome was calculated from the following formula.

(Ratio of uptake amount)[%]=(Amount of uptake of each modified liposome)/(Amount of uptake of unmodified liposome)×100

Figure 4:
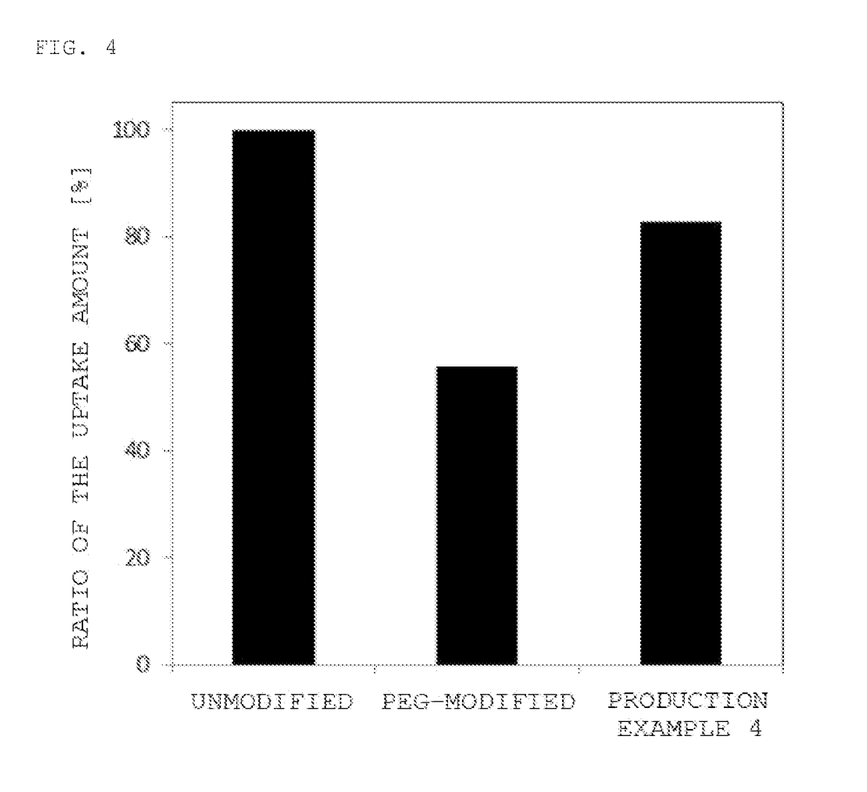
FIG. 4 is a graph illustrating a measurement result of the amount of uptake of a fluorescent substance-encapsulated liposome modified using the 2 w/v % PBS solution of the amphiphilic compound (polymer) prepared in Production Example 4 into HepG2 cells in comparison with unmodified liposome and PEG modified liposome.

As a result, as illustrated in FIG. 4, the amount of uptake into cells was significantly reduced in the PEG-modified liposome as compared with the unmodified liposome; whereas no significant difference was observed in the uptake amount of liposomes modified with an amphiphilic compound (polymer) as compared with unmodified liposomes.

This application is based on Japanese Patent Application No. 2019-067826 filed on Mar. 29, 2019, the disclosure of which is incorporated in its entirety by reference.

The invention claimed is:

1. An amphiphilic compound comprising:
a moiety (I) including a constitutional unit (A); and
a hydrocarbon group having 8 or more carbon atoms,
wherein the constitutional unit (A) includes a constitutional unit represented by chemical formula (1):

wherein $R^1$ represents a hydrogen atom or a methyl group, and X represents —C(=O)—O—, —C(=O)—NH—, —O—, —CH$_2$O—, or —CH$_2$CH$_2$O—,
the hydrocarbon group having 8 or more carbon atoms is bonded to the moiety (I) via a divalent bonding group containing a group selected from the group consisting of —S—, —S—C(=S)—, —S—C(=S)—S—, —S—C(=S)—N(—R$_a$)—, —S—C(=S)—O—, —S—R$_b$—C(=O)—O—, —S—R$_b$—C(=O)—N(—R$_a$)—, —S—R$_b$—O—, —S—R$_b$—O—C(=O)—, and —N(—R$_a$)—C(=O)—, wherein R$_a$ is a hydrogen atom or a hydrocarbon group having 1 to 30 carbon atoms, and R$_b$ is a hydrocarbon group having 1 to 30 carbon atoms.

2. The amphiphilic compound according to claim 1, wherein the moiety (I) consists of a polymer having the constitutional unit (A).

3. The amphiphilic compound according to claim 1, wherein the hydrocarbon group having 8 or more carbon atoms has 8 to 50 carbon atoms.

4. The amphiphilic compound according to claim 1, wherein the hydrocarbon group having 8 or more carbon atoms is present as a portion of a lipid, and the lipid is bonded to the moiety (I) having the constitutional unit (A) via the divalent bonding group.

5. The amphiphilic compound according to claim 1, wherein a proportion of the constitutional unit (A) is 1 to 100% by mass relative to a total mass of the moiety (I).

6. The amphiphilic compound according to claim 1, wherein the hydrocarbon group is present as a portion of a lipid and a molecular weight of the lipid is 2000 or less.

7. The amphiphilic compound according to claim 1, wherein a number average molecular weight (Mn) of the moiety (I) including the constitutional unit (A) is 1000 to 90000.

8. A medical resin composition comprising:
the amphiphilic compound according to claim 1.

9. A liposome comprising:
the amphiphilic compound according to claim 1.

10. A pharmaceutical additive comprising:
the amphiphilic compound according to claim 1.

11. A pharmaceutical additive comprising:
the medical resin composition according to claim 8.

12. A pharmaceutical additive comprising:
the liposome according to claim 9.

13. A pharmaceutical additive according to claim 10, wherein the pharmaceutical additive is a carrier for holding a medicine.

14. A pharmaceutical additive according to claim 11, wherein the pharmaceutical additive is a carrier for holding a medicine.

15. A pharmaceutical additive according to claim 12, wherein the pharmaceutical additive is a carrier for holding a medicine.

16. The amphiphilic compound according to claim 1, wherein a molecular weight of the hydrocarbon group having 8 or more carbon atoms is in a range of 100 or more and 5000 or less.

17. The amphiphilic compound according to claim 1, wherein a proportion of a molecular weight of the hydrocarbon group having 8 or more carbon atoms is 0.2 to 20% relative to a molecular weight of the amphiphilic compound.

* * * * *